United States Patent [19]

Bradford

[11] Patent Number: 5,788,976
[45] Date of Patent: Aug. 4, 1998

[54] METHOD FOR EFFECTING BONE REPAIR

[75] Inventor: David S. Bradford, San Francisco, Calif.

[73] Assignee: WBK, Inc., Diablo, Calif.

[21] Appl. No.: 600,284

[22] Filed: Feb. 12, 1996

[51] Int. Cl.⁶ ............................... A61F 13/00; A61F 2/00
[52] U.S. Cl. ...................... 424/422; 424/426; 424/423; 604/16; 604/66; 606/86; 607/51; 602/51
[58] Field of Search .................................. 424/422, 426, 424/423, 520, 548, 549, 577, 283; 606/86; 607/51; 604/66, 16; 602/57

[56] References Cited

U.S. PATENT DOCUMENTS

| | | | |
|---|---|---|---|
| 4,196,218 | 4/1980 | Thiele | 424/318 |
| 4,434,094 | 2/1984 | Seyedin et al. | 260/112 |
| 4,472,840 | 9/1984 | Jefferies | 623/16 |
| 4,553,272 | 11/1985 | Mears | 623/1 |
| 4,563,489 | 1/1986 | Urist | 524/21 |
| 4,609,551 | 9/1986 | Caplan et al. | 424/95 |
| 4,620,327 | 11/1986 | Caplan et al. | 632/10 |
| 4,642,120 | 2/1987 | Nevo et al. | 623/16 |
| 4,678,470 | 7/1987 | Nashef et al. | 623/16 |
| 4,743,259 | 5/1988 | Bolander et al. | 623/16 |
| 4,795,467 | 1/1989 | Piez et al. | 623/16 |
| 4,950,296 | 8/1990 | McIntyre | 623/16 |
| 4,990,333 | 2/1991 | Lane et al. | 424/551 |
| 5,035,901 | 7/1991 | Anderson et al. | 424/573 |
| 5,067,963 | 11/1991 | Khouri et al. | 623/16 |
| 5,073,373 | 12/1991 | O'Leary et al. | 424/422 |
| 5,120,656 | 6/1992 | O'Leary et al. | 435/268 |
| 5,133,756 | 7/1992 | Bauer et al. | 623/16 |
| 5,167,961 | 12/1992 | Lussi et al. | 424/423 |
| 5,204,106 | 4/1993 | Schepers et al. | 424/423 |
| 5,236,456 | 8/1993 | O'Leary et al. | 623/16 |
| 5,244,577 | 9/1993 | Notoya et al. | 210/641 |
| 5,282,861 | 2/1994 | Kaplan | 623/16 |
| 5,284,655 | 2/1994 | Bogdansky et al. | 424/422 |
| 5,290,558 | 3/1994 | O'Leary et al. | 424/422 |
| 5,314,476 | 5/1994 | Prewett et al. | 623/16 |
| 5,356,629 | 10/1994 | Sander et al. | 424/422 |
| 5,403,825 | 4/1995 | Lagarde et al. | 514/21 |

*Primary Examiner*—Marian C. Knode
*Assistant Examiner*—Ali R. Salimi

[57] ABSTRACT

A method is provided for the repair of a bone defect in a patient which employs a bone growth-stimulating composition derived from healthy cancellous bone.

8 Claims, No Drawings

METHOD FOR EFFECTING BONE REPAIR

BACKGROUND OF THE PRESENT INVENTION

The present invention is directed to a method and composition for healing bone defects by promoting new bone growth.

It is frequently necessary to effect repair of bone defects caused by injury or disease (including infection, malignancy or developmental malfunction). Large bone defects generally require the use of bone implant material which ultimately becomes an integral part of the healed bone or serves as a resorbable matrix for new bone growth. See, for example, U.S. Pat. Nos. 4,472,840; 4,553,272; 4,678,470; 4,743,259; 4,950,296; 5,073,373; 5,120,656; 5,153,756; 5,167,961; 5,204,106; 5,236,456; 5,282,861; 5,284,655; 5,290,558; 5,314,476; and 5,356,629.

However, the use of bone graft materials in reconstruction or repair procedures is not without disadvantage. To the extent such materials consist of non-autogenous materials, stringent medical standards must be met and regulatory approval gained prior to use to safeguard the health of the patient. Further, the possibility of incompatibility of non-autogenous implanted material always exists. To avoid incompatibility and possible contamination, the non-autogenous implant materials are rendered substantially inert prior to use. This, however, destroys those protein factors normally present in bone which encourage new bone growth. In an attempt to address deficiencies associated with the use of nonautogenous materials, it has been proposed to provide live autogenous skeletal replacement parts through muscle flap molding and osteoinduction. See U.S. Pat. No. 5,067,963. See also, Habel et al., "Autologous Corticocancellous Bone Paste for Long Bone Discontinuity Defects: An Experimental Approach", *Annals of Plastic Surgery*, Vol. 15, No. 2, pp 138–142 (August 1985) which discloses a procedure whereby autogenous bone is granulated into a pastelike material and combined with autogenous blood for repair of long bone defects in dogs.

One of the most prevalent types of bone repair involves the fusion of several spinal vertebrate together to minimize movement of one or more sections of the spine. This procedure generally involves the removal of bone graft material from the patient's ilium. This material is applied to the spinal vertebrate in need of stabilization after decortication of portions of the spine. This procedure, while practiced in essentially the same manner for the past 75 years or so, is not without its disadvantages. The removal of the bone graft material from the ilium constitutes a major procedure, involving the exposure of the ilium through the patient's skin and muscle tissue as well as the removal of significant portions of the ilium. Frequently, the patient suffers from significant pain and discomfort from this portion of the procedure in addition to the pain and discomfort associated with the spinal fusion procedure itself.

It has thus been a goal of the medical community to provide a method for bone repair which both avoids problems of incompatibility and possible rejection of a bone repair material. It is also a goal to reduce the trauma and extent of incapacitation suffered by a patient during such a procedure. For instance, the repair of spinal column bone defects frequently requires a healing period of three months or so. During that time the patient is incapacitated, causing significant disruption of the patient's life and discomfort during rehabilitation. This is especially the case since the patient has been subjected to major invasive procedures on both the hip and back portions of the body. It is thus a goal to provide a method to repair the spine while at the same time minimizing the trauma suffered by the patient and minimizing the time required for recovery.

In order to assist in promoting the growth of new bone in bone repair procedures, the use of various bone growth promoting substances has been proposed. See, for example, U.S. Pat. Nos. 4,434,094; 4,563,489; 4,609,551; 4,620,327; 4,642,120; 4,795,467; 5,035,901; 5,244,577; and 5,403,825. However, such substances still suffer from the deficiency that they are generally non-autogenous. It is thus desirable to provide an autogenous material which may be used in bone repair procedures to assist in promoting bone growth.

OBJECTS AND SUMMARY OF THE PRESENT INVENTION

It is accordingly an object of the present invention to provide an improved method for the repair of bone defects in a patient by use of an autogenous material.

It is still another object of the present invention to provide an improved method for the repair of spinal bone defects.

It is yet another object of the present invention to provide an improved method for the recovery of bone graft material from the ilium.

It is yet another object of the present invention to provide an autogenous bone repair material which may be employed to heal injured or defective bone.

In accordance with the present invention, there is thus provided a bone growth stimulating composition for application to a bone defect site to promote new bone growth at the site, said composition comprising a water-insoluble lipid-containing fraction produced by the method of:

(1) recovering a portion of the cancellous bone of a patient in finely divided form together with all constituent components thereof including finely divided bone, blood, marrow and bone stem cell elements;

(2) forming an admixture of the finely divided portion of cancellous bone recovered in step (1) with a sterile aqueous liquid either simultaneously with said recovery or subsequent thereto;

(3) centrifuging said admixture of step (2) under sterile conditions to cause said admixture to separate into differing constituent portions including an uppermost water-insoluble lipid-containing fraction and a lowermost layer of bone particles, stem cells and other bone marrow elements; and (4) recovering said water-insoluble lipid-containing fraction optionally together with the lowermost layer of bone particles.

In accordance with the present invention there is also provided a method for effecting bone repair at a bone defect site in a patient, said method comprising contacting bone in need of repair at said bone defect site with a water-insoluble, lipid-containing composition produced by the method of:

(1) recovering a portion of healthy cancellous bone of said patient in finely divided form together with all constituent components thereof including finely divided bone, blood, marrow and bone stem cell elements;

(2) forming an admixture of the finely divided portion of cancellous bone recovered in step (1) with a sterile aqueous liquid either simultaneously with said recovery or subsequent thereto;

(3) centrifuging said admixture of step (2) under sterile conditions to cause said admixture to separate into differing constituent portions including an uppermost water-insoluble lipid-containing fraction and a lowermost layer of bone particles, stem cells and other bone marrow elements; and (4) recovering said water-insoluble lipid-containing fraction optionally together with the lowermost layer of bone particles for use in said bone repair.

In a preferred embodiment, the healthy cancellous bone of the patient resides between the two tables of the patient's iliac crest, and is recovered in finely divided form by drilling into the cancellous bone of the ilium between the two tables percutaneously or through minimal incision in the patient's skin.

In a further preferred embodiment, the method of bone repair comprises a spinal fusion procedure which involves use of the water-insoluble, lipid-containing composition produced by the above method as well as recovered bone particles.

DETAILED DESCRIPTION OF THE PRESENT INVENTION

The present invention is directed to the use of a novel autogenous material to encourage the growth of new bone during bone reconstruction or repair.

Bone tissue exists in two forms; i.e., compact bone and spongy or cancellous bone. In compact bone, the lamellae of the bone are concentrically arranged around an elongated and narrow marrow space containing blood vessels and connective tissue. By contrast, cancellous bone consists of a three dimensional lattice partially enclosing many interconnecting and communicating spaces filled with bone marrow. The cancellous bone located between the inner and outer tables of the ilium has been used for years as a source of autogenous bone repair material for use in bone reconstruction or fusion.

It is with respect to cancellous bone that the present invention is directed. It has been found possible to minimize trauma to a patient during removal of autogenous cancellous bone graft material from the patient by drilling out and recovering respective portions of the cancellous bone through an incision in the patient's skin. This avoids the need (as has been normal practice to date) to expose the ilium, stripping the muscles from the outer layer, and remove bone graft material from the ilium. In accordance with the present invention, a surgical drill is then used to enter the ilium between the inner and outer tables of the iliac crest either percutaneously or through minimal incision in the patient's skin. Portions of the cancellous bone within the ilium are then drilled out and removed for recovery under sterile conditions. All constituent portions of the drilled out bone are recovered, including finely divided bone particles, blood, marrow and bone stem elements, etc. These components are recovered under suction and collected in a sterile container. During drilling, the bone is preferably irrigated with a sterile irrigating fluid to assist in the collection of the bone elements. A filter may be employed to ensure retention of all bone elements.

Once collected, the admixture of irrigating fluid and collected bone elements and associated material is subjected to centrifugation under sterile conditions to separate the admixture into differing constituent portions. It has been found that low intensity centrifugation at 2000-2500 rpm or so is suitable. However, the centrifugation speed employed is not critical and need only be sufficient to cause the desired separation to occur. An uppermost water-insoluble lipid-containing fraction is formed upon centrifugation of the admixture and constitutes the novel composition of the present invention. This fraction is separately recovered and may be used to promote bone growth during bone repair or reconstruction. The lipid-containing layer exhibits substantial physical integrity and may be lifted from the centrifuge tube as a unitary layer. A lowermost layer of bone particles and stem cells and other bone marrow elements also results.

The novel autogenous composition of the present invention may be employed in a variety of ways. In its simplest embodiment, the composition may be applied to the surface of bone graft material prior to implantation of same so as to contact adjacent live bone tissue (by means of a spatula, etc.) upon implantation to promote bone growth. Exemplary bone repair materials include both autogenous and donor bone tissue and other suitable bone implant materials. When used in connection with bone grafts, conventional bone grafting procedures are employed. By way of brief description, damaged sections of the patient's bone are removed. Bone grafting material is inserted in place of the damaged bone. Standard means of attachment are employed, such as wires, screws intramedullary rods, casts, or other fixation means, in order to maintain the position of the grafting material during the healing process.

If used in association with spinal fusion, the material may be placed on decorticated sections of the patient's spinal column either in admixture with autogenous bone particles (recovered either from the ilium as the bottommost layer in the centrifuge tube or during the decortication procedure) or layered on top of such bone particles which are placed over the decortication site.

By way of alternative embodiment, a bone defect site may be packed with a viscous paste formed of the novel composition of the present invention together with suitable bone repair material in finely divided form (such as bone powder or synthetic bone repair material). Such bone material can be recovered from the centrifuged material (as recovered bone particles as a bottommost layer) or can be supplied from another source (e.g., as demineralized bone particles).

If used in connection with demineralized bone particles or other suitable bone replacement material, the composition can be used for a variety of surgical procedures including the repair of multiple and compound fractures, joint reconstructions, repairs of the vertebral column including spinal fusion and internal fixation, tumor surgery, repair of spinal injuries, alveolar ridge augmentation and reconstruction, inlay bone grafts, etc.

By way of yet another embodiment, the material can be used as an injectable substance to stimulate bone growth or to counteract bone loss due to injury or disease. The novel composition of the present invention may be used in injectable form for delivery by percutaneous injection directly to a fracture site to assist in treatment of the fracture. For instance, pins are frequently used to stabilize fractures of bones. Upon removal of the pin(s), a tunnel remains into which the novel composition may be injected to assist in stimulating bone growth.

The method of the present invention may be described as follows in connection with spinal fusion. The patient's ilium is prepped routinely as per surgery. At the time of the spinal fusion procedure or bone reconstructive procedure (requiring bone grafting), a small incision measuring approximately one inch in length is made over the ilium (posterior superior iliac crest or the anterior superior iliac crest). The crest is exposed through this incision. A small (1–2 cm) window is made into the ilium and the superficial portion of the cancellous bone is curetted with a large curette without violating the inner-outer cortices of the ilium. A surgical drill (having a 3/16–1/4" burr size) is then placed into the hole with irrigation carried out as required. The cancellous bone is drilled out from between the inner and tables of the ilium and retrieved into a suction trap. Irrigation with Ringers lactate is carried out in sufficient quantity to retrieve not only the finely divided bone particles but also the blood, marrow and stem cell elements contained in the cancellous bone. Copious amounts of bone, along with the marrow elements, are obtained with this technique, all of which are collected in the suction trap container. Up to four 50–75 cc collection vessels are employed to collect the recovered material. Under the sterile conditions of the operating room, the suction trap container(s) is then placed into a centrifuge and centrifuged for approximately five minutes at 2000–2500 rpm. This causes the collected admixture to stratify into various component lowermost layer of bone, intermediate irrigating liquid and serum layer and an uppermost water-insoluble lipid-containing layer. This uppermost layer has a gel-like consistency. This layer may be easily recovered (by being lifted from the aqueous layer) and placed over a bed of bone particles recovered as the lowermost layer in the centrifuge tube which have been placed over the previously-decorticated bone area to be fused. Following the bone harvesting the ilium incision is closed in a standard fashion.

Advantages attendant the described technique for bone repair procedures such as spinal fusion include minimal blood loss since the iliac crest does not have to be stripped of soft tissue and muscle attachments for bone retrieval. The procedure takes considerably less time than a standard iliac crest bone grafting technique. Furthermore, the amount of bone retrieved is substantially greater than previously described grafting techniques in that all of the bone and marrow is salvaged and not just the long strips which are obtained with routine bone grafting techniques. Using centrifuge techniques, the aspirated marrow, cells, bone and associated biological substances can be collected for centrifugation in a sterile closed centrifuge system.

Further, during prior art autogenous bone graft and spinal reconstruction procedures, large amounts of small bone particles together with associated marrow elements were lost, especially during the spinal decortication procedure. It was thus one disadvantage that only a portion of the autogenous bone reconstructive materials were available for use in bone repair. The present invention addresses this problem by aspirating and collecting substantially all of the autogenous material for use in bone repair or reconstruction.

What is claimed is:

1. A method for promoting new bone growth in a patient in need of bone repair of a bone defect site, said method comprising contacting bone in need of repair at said bone defect site with a water-insoluble, lipid-containing composition produced by the method of:

(1) recovering a portion of the cancellous bone of said patient in finely divided form together with all constituent components thereof including blood, marrow and bone stem cell elements;

(2) forming an admixture of the finely divided portion of cancellous bone recovered in step (1) with a sterile aqueous liquid either simultaneously with said recovery or subsequent thereto;

(3) centrifuging said admixture of step (2) to cause said admixture to separate into differing constituent portions comprising an uppermost water-insoluble lipid-containing fraction and a lowermost bone-containing fraction; and (4) recovering said water-insoluble lipid-containing fraction optionally in association with the lowermost bone-containing fraction for use in said bone repair.

2. The method of claim 1 wherein said portion of said cancellous bone of said patient is recovered by drilling into the cancellous portion of a bone of said patient.

3. The method of claim 2 wherein said cancellous bone is recovered from the ilium of said patient.

4. The method of claim 1 wherein said composition is applied to portions of a bone implant which is caused to contact adjacent portions of bone of said patient to repair a bone defect.

5. In a method of repairing a defect in a patient's spinal column by spinal fusion wherein a portion of the spinal column is decorticated, bone graft material applied to the decorticated portion and the spinal column immobilized to permit growth of new bone, the improvement wherein said bone graft material is applied together with a water-insoluble, lipid-containing composition produced by the method of:

(1) recovering a portion of the cancellous bone of said patient in finely divided form together with all constituent components thereof including blood, marrow and bone stem cell elements by drilling into a cancellous bone of said patient;

(2) forming an admixture of the finely divided portion of cancellous bone recovered in step (1) with a sterile aqueous liquid either simultaneously with said recovery or subsequent thereto;

(3) centrifuging said admixture of step (2) to cause said admixture to separate into differing constituent portions comprising an uppermost water-insoluble lipid-containing fraction and a lowermost bone-containing fraction; and (4) recovering said water-insoluble lipid-containing fraction optionally together with said lowermost bone-containing layer for use in said bone repair.

6. The method of claim 5 wherein cancellous bone is recovered from the ilium of said patient.

7. The method of claim 6 wherein said cancellous bone is recovered by drilling into the ilium between the inner and outer tables of the ilium.

8. The method of claim 5 wherein said lipid-containing composition is applied to said decorticated portion of said spinal column together with bone particles recovered as said lowermost fraction.

* * * * *